United States Patent
Andre et al.

(10) Patent No.: US 6,506,555 B1
(45) Date of Patent: Jan. 14, 2003

(54) USE OF HIV PROTEASE INHIBITING COMPOUNDS

(75) Inventors: Patrice Andre, Rennes (FR); Vincent Lotteau, Rennes (FR); Paul Klenerman, Oxford (GB); Rolf Zinkernagel, Zumikon (CH); Marcus Groettrup, St Gallen (CH)

(73) Assignees: Institut National de la Sante et de la Recherche Medicale (Inserm), Paris, Cedex (FR); Biomerieux, Marcy L'Etoile (FR)

( * ) Notice: Subject to any disclaimer, the term of this patent is extended or adjusted under 35 U.S.C. 154(b) by 0 days.

(21) Appl. No.: 09/719,140

(22) PCT Filed: Jun. 11, 1999

(86) PCT No.: PCT/FR99/01391

§ 371 (c)(1),
(2), (4) Date: Jun. 19, 2001

(87) PCT Pub. No.: WO99/63998

PCT Pub. Date: Dec. 16, 1999

(30) Foreign Application Priority Data

Jun. 11, 1998 (FR) .............................................. 98 07373

(51) Int. Cl.[7] .......................... C12Q 1/70; A61K 39/12; A01N 43/58
(52) U.S. Cl. ................... 435/5; 424/204.1; 514/254.02; 514/254.11; 514/249
(58) Field of Search ...................... 514/254.02, 254.11, 514/249; 544/367, 377, 349; 435/5; 424/204.1, 228.1, 275.1, 277.1

(56) References Cited

FOREIGN PATENT DOCUMENTS

| DE | 43 07 883 A | 9/1993 |
| EP | 0 432 694 A | 6/1991 |
| EP | 0 432 695 A | 6/1991 |
| WO | WO 94 14436 A | 7/1994 |
| WO | WO 96 13266 A | 5/1996 |
| WO | WO 96 26734 A | 9/1996 |
| WO | WO 98 52571 A | 11/1998 |

OTHER PUBLICATIONS

Rutschmann et al., Impact of Treatment with HIV Protease Inhibitors on Hepatitis C Viremia in Patients Coinfected with HIV, J. Infectious Diseases, Mar. 1998; 177:783–785.*

Kotler, et al., Effect of combination antiretroviral therapy upon rectal mucosal HIV RNA burden and mononuclear cell apoptosis, AIDS, 1998, 12:597–604.*

Conant et al., Reduction of Kaposi's sarcoma lesions following treatment of AIDS with ritonavir, AIDS, 1997, 11:1300–1301.*

(List continued on next page.)

Primary Examiner—Hankyel T. Park
Assistant Examiner—Stacy S. Brown
(74) Attorney, Agent, or Firm—Larson & Taylor PLC

(57) ABSTRACT

The invention relates to the use of at least one compound that inhibits HIV (human immunodeficiency virus) protease, selected from ritonavir, saquinavir or one of the pharmaceutically acceptable salts thereof, in association with a pharmaceutically acceptable vehicle for the production of a medicament to modulate proteasome.

4 Claims, 10 Drawing Sheets

OTHER PUBLICATIONS

Sloand et al., HIV–1 Protease inhibitor modulates activation of peripheral blood, Blood, Nov. 1997, vol. 90, No. 10, Suppl. 1 part 1 p. 577A.*

Mauss et al., Influence of HIV protease inhibitors of HCV load in individuals with HIV and HCV Coinfection, Abstracts of the Interscience Conference on Antimicrobial Agents and Chemotherapy, Oct. 1997, 37:218.*

Berthelot et al., Dramatic Cutaneous Psoriasis Improvement in a Patient, Archives of Dermatology, Apr. 1997, 133:531.*

Mauss, S. (1) et al.: "Influence of HIV protease inhibitors on hepatitis C viral load in individuals with HIV and HCV coinfection." Abstracts of the Interscience Conference on Antimicrobial Agents and Chemotherapy, (1997) vol. 37, pp. 218. Meeting Info.: 37$^{th}$ Interscience Conference on Antimicrobial Agents and Chemotherapy Toronto, Ontario, Canada Sep. 28–Oct. 1, 1997 TCA, XP002095185—The whole document.

Autran, B. et al.: "Positive effects of combined antiretroviral therapy on CD4+ T cell homeostasis and function in advanced HIV disease"—Science (Washington, D.C.) (1997), 277(5322), 112–116 Coden: Scieas: ISSN 0036–8075, XP002095186—The whole document.

Badley, Andrew D. et al: "In vivo analysis of Fas/FasL interactions in HIV–infected patients"—J. Clin. Invest. (1998), 102(1), 79–87, XP002121453—The whole document.

Sloand, E.M. (1) et al: "HIV–1 protease inhibitor modulates activation of peripheral blood derived CD4+T–cells and decreases their susceptibility to apoptosis in vitro and in vivo." Blood, (Nov. 15, 1997) vol. 90, No. 10 Suppl. 1 Part 1, pp. 577A, Meeting Info.: 39$^{th}$ Annual Meeting of The American Society of Hematology San Diego, California, USA Dec. 5–9, 1997 The American Society of Hematology., XP002121454—The whole document.

Kotler D.P. et al: "Effect of combination antiretroviral therapy upon rectal mucosal HIV RNA burden and mononuclear cell apoptosis." AIDS, (Apr. 16, 1998) 12/6 (597–604)., XP002121455—The whole document.

Diz Dios P. et al: "Regression of AIDS–related Kaposi's sarcoma following ritonavir therapy." Oral Oncology, (1998), 34/3 (236–238)., XP002121456—The whole document.

Parra R. et al.: "Regression of invasive AIDS–related Kaposi's sarcoma following antiretroviral therapy." Clinical Infectious Diseases, (1998) 26/1 (218–219)., XP002121457—The whole document.

M.A. Conant et al: "Reduction of Kaposi's Sarcoma Lesions Following Treatment of AIDS with Ritonavir"—AIDS, vol. 11, No. 10, 1997, pp. 1300–1301, XP002121458—The whole document.

Reed, J. Brian et al: "Regression of cytomegalovirus retinitis associated with protease–inhibitor treatment in patients with AIDS"—AM. J. Ophthalmol. (1997), 124(2), 199–205, XP002121459—The whole document.

Andre, Patrice et al: "An inhibitor of HIV–1 protease modulates proteasome activity, antigen presentation, and T–cell responses"—Proc. Natl. Acad. Sci. U.S.A. (1998), 55(22), 13120–13124 Coden: PNASA6; ISSN: 0027–8424, XP002095181—The whole document.

Berthelot P et al: "Dramatic cutaneous psoriasis improvement in a patient with the human immunodeficiency virus treated with 2', 3'–dideoxy, 3'–thyacytidine correction of 2', 3'–dideoxycytidine! and ritonavir letter! published erratum appears in Arch Dermatol 1998—Apr. 134(4): 452!."— Archives of Dermatology (Apr. 1997) 133 (4) 531. Journal Code: 6WU. ISSN: 0003–987X, XP002095182 United States—The whole document.

Carr, Andrew (1) et al: "Restoration of immunity to chronic hepatitis B infection in HIV–infected patient on protease inhibitor." Lancet (North American Edition), (1997) vol. 349, No. 9057, pp. 995–996. ISSN: 0099–5535.. XP002095183—The whole document.

O.T. Rutschmann et al.: "Impact of treatment with Human Immunodeficiency Virus (HIV) Protease Inhibitors on Hepatitis C viremia in Patients Coinfeted with HIV"—The Journal of Infectious Disease, vol. 177, No. 3, Mar. 1998 pp. 783–785, XP002059184—The whole document.

* cited by examiner

SEQUENCE LISTING

```
<160> NUMBER OF SEQ ID NOS: 2

<210> SEQ ID NO 1
<211> LENGTH: 9
<212> TYPE: PRT
<213> ORGANISM: Lymphocytic choriomeningitis virus

<400> SEQUENCE: 1

Lys Ala Val Tyr Asn Phe Ala Thr Cys
1               5

<210> SEQ ID NO 2
<211> LENGTH: 9
<212> TYPE: PRT
<213> ORGANISM: Lymphocytic choriomeningitis virus

<400> SEQUENCE: 2

Glu Gln Pro Gln Asn Gly Phe Ile His
1               5
```

USE OF HIV PROTEASE INHIBITING COMPOUNDS

FIELD OF THE INVENTION

The subject of the present invention is the therapeutic use of a human immunodeficiency virus (HIV) protease inhibiting compound as proteasome modulator.

DESCRIPTION OF RELATED ART

Proteasome, a central enzymatic system in protein degradation both in the cytosol and in the nucleus, is a complex having multiple peptidase activities. One of its functions is the generation of small peptides by intracellular proteolysis, these small peptides being presented to the T lymphocytes so as to initiate immune responses.

It has been shown that peptide aldehydes are proteasome inhibitors and block the degradation of most cellular proteins and the generation of the peptides presented at the surface of antigen presenting cells, in association with the molecules of the major histocompatibility complex class I (Rock et al., Cell, 1994, vol. 78, 761–771). Several patent applications disclose, moreover, proteasome inhibitors which can be used in the treatment of diseases in which a loss of body mass is observed (WO 95/24 914), diseases resulting from cell proliferation (WO 98/13 061) and more generally diseases involving the proteolytic function of the proteasome, such as in particular inflammatory diseases and cancers (WO 96/32 105; WO 96/13 266).

BRIEF SUMMARY OF THE INVENTION

The subject of the present invention is the use of at least one human immunodeficiency virus (HIV) protease inhibiting compound chosen from ritonavir, saquinavir, or one of their pharmaceutically acceptable salts, in combination with a pharmaceutically acceptable vehicle, for the manufacture of a medicament intended for modulating the proteasome.

Surprisingly, the authors of the present invention have discovered that certain human immuno-deficiency virus (HIV) protease inhibiting compounds exhibit a modulatory action on the activity of the proteasome.

They are:

ritonavir, and its pharmaceutically acceptable salts, a proprietary medicinal product containing ritonavir as active ingredient, being Norvir® (Abbott);

and saquinavir, and its pharmaceutically acceptable salts, a proprietary medicinal product containing saquinavir, in the form of saquinavir mesylate as active ingredient, being Invirase® (Roche).

Ritonavir, saquinavir or their salts may be used alone or in the form of a mixture. The combination of ritonavir and saquinavir is particularly advantageous because it makes it possible to enhance the pharmacokinetics of saquinavir, whose degradation is slowed down by the presence of ritonavir.

These inhibitors (described in Patent Applications WO 94/14 436 and EP 432 695) of the human immunodeficiency virus (HIV) protease are widely used in the treatment of AIDS. These compounds block viral replication by specifically inhibiting the viral protease which allows cleavage of the viral protein precursors to mature viral proteins. The tritherapy using such a protease inhibitor combined with two nucleoside analogues is thus currently the most effective strategy for the treatment of an HIV infection.

The subject of the present invention is therefore the use of at least one human immuno-deficiency virus (HIV) protease inhibiting compound chosen from ritonavir, saquinavir, or one of their pharmaceutically acceptable salts, in combination with a pharmaceutically acceptable vehicle, for the manufacture of a medicament intended for modulating the proteasome.

The authors of the present invention have thus discovered that ritonavir and saquinavir inhibited the "chymotrypsin-like" activity of the proteasome and increased the "trypsin" activity of the proteasome.

The modulation of the proteasome makes it possible to act on a number of events "downstream".

The authors of the present invention have more particularly demonstrated that these human immuno-deficiency virus (HIV) protease inhibiting compounds exhibiting a modulatory action on the activity of the proteasome made it possible to modify the presentation of antigens in combination with the major histo-compatibility complex class I (MHC1), at the surface of the cells and consequently inhibited or modified the activation of the $CD8^+$ cytotoxic T lymphocytes. These compounds therefore have the crucial advantage of not directly influencing the activity of the helper T lymphocytes at therapeutic concentrations. Human immunodeficiency virus (HIV) protease inhibiting compounds exhibiting a modulatory action on the activity of the proteasome are therefore particularly useful for the prevention and/or treatment of conditions in which an inadequate response, for example an excessive response, of the $CD8^+$ cytotoxic T lymphocytes is observed. More generally, the conditions aimed at are those for whose treatment a modulation (such as in particular a decrease) in the immune response provided by the $CD8^+$ cytotoxic T lymphocytes is sought.

The HIV protease inhibiting and proteasome modulating compounds according to the invention exhibit, moreover, an apoptosis modulating activity, a consequence of the modulation of the proteasome (Nagata et al., 1997, Cell, 88:355–365: Ruggieri et al., 1997, Virology, 229:68–76: WO 98/13 061).

Among the conditions for which it is advantageous to modulate the activity of the proteasome, there may be mentioned in particular inflammatory diseases, infectious diseases and/or those for whose treatment modulation or control of apoptosis is desired. Those more particularly aimed at are:

autoimmune diseases, such as type 1 diabetes, multiple sclerosis, psoriasis, contact hypersensitivity or rheumatoid arthritis;

viral conditions, in particular infections with noncytopathogenic viruses such as infections with the hepatitis viruses, in particular the hepatitis B virus and the hepatitis C virus;

transplant rejections, and diseases resulting from abnormal cell proliferation, such as cancers.

It is understood that acquired immunodeficiency syndrome (AIDS) is not a condition aimed at since the decrease in the number of $CD8^+$ T lymphocytes is not desired in the treatment of this syndrome.

The subject of the present invention is also a method of screening human immunodeficiency virus (HIV) protease inhibiting compounds, consisting in testing the said compounds for their capacity to modulate the activity of the proteasome.

This includes in particular screening known HIV protease inhibitors, such as in particular the inhibitors described in Patent Applications WO 94/14 436 and EP 432 695 for the evaluation of their proteasome activity modulating action.

Such a screening test is acceptable to persons skilled in the art. The HIV protease inhibiting compounds may in particular be tested on isolated proteasomes by determining the capacity of these compounds to modulate the peptidase activity of the proteasome (Cerundolo V et al., Eur. J. Immunol., 27, 336–341 (1997); Groettrup M. et al., J. Biol. Chem. 270, 23808–23815 (1995)). It is also possible to carry out functional tests which determine the capacity of these compounds to modulate the presentation of the antigens to T lymphocyte clones (Gervois N. et al., J. Exp. Med., 183, 2403–2407 (1996); York et al., Annu. Rev. Immunol., 14, 369–396 (1996); Rock K. L. et al., Proc. Natl. Acad. Sci. USA 94, 10850–10855 (1997)).

The medicament prepared in accordance with the present invention and containing at least one proteasome activity modulating compound, in combination with a pharmaceutically acceptable vehicle, may be in the form of a pharmaceutical composition intended for administration by the oral route, for example in the form of a tablet, a gelatin capsule, an oral solution and the like, or by the rectal route, for example in the form of a suppository. It may also be administered by the parenteral route, in particular in the form of an injectable solution, in particular by the intravenous, intradermal or subcutaneous route, and the like. It may finally be in the form of a pharmaceutical composition intended for topical administration, such as an ointment. Such a formulation is particularly advantageous in the case of the treatment of psoriasis and of contact hypersensitivities.

The medicament prepared in accordance with the present invention preferably contains from 1 to 2000 mg, preferably from 100 to 500 mg, of the said compound exhibiting a proteasome activity modulating action.

The present invention also relates to a method of therapeutic treatment in which a therapeutically effective quantity of at least one HIV protease inhibiting compound chosen from ritonavir, saquinavir or one of their pharmaceutically acceptable salts, alone or in the form of a mixture, in combination with a pharmaceutically acceptable vehicle, is administered to a patient suffering from a condition for whose treatment modulation of the proteasome is desired.

The dosage depends on the seriousness of the condition, the age and weight of the patient. It may be in particular from 100 to 1500 mg per day, preferably from 600 to 1200 mg per day.

The figures and the examples below illustrate the invention without limiting it.

BRIEF DESCRIPTION OF THE DRAWINGS

Legend to the Figures

DETAILED DESCRIPTION OF THE INVENTION

The present invention is described below with reference to the following examples which do not limit the scope of the present invention in any way.

EXAMPLE 1

Effect of Ritonavir on the Activity of the Cytotoxic T Lymphocytes In Vivo

Figure 1A:
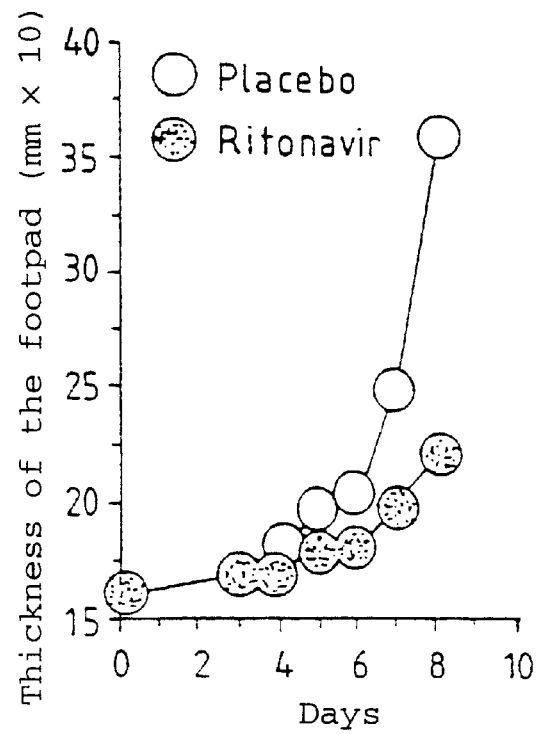
FIG. 1A represents the thickness of the footpad of mice as a function of time, the mice treated with ritonavir being compared with control mice.

1. Inhibition of the Swelling of Mouse Footpads After Infection with the LCMV Virus Method:

The authors of the present invention used the murine model of LCMV (lymphocytic choriomeningitis virus), given that this noncytopathogenic virus causes an infection in which the cytotoxic T lymphocytes are responsible both for the initial control of viral replication and for the immunopathology induced by the virus. C57BL/6 mice are infected at the level of the footpad on day D0 (300 pfu-plaque forming units- of LCMV-WE provided by F. Lehmann-Grube, Hambourg) and the swelling of the footpad is measured over time. Ritonavir (1.25 mg/mouse/day dissolved in 10% of alcohol, 90% of phosphate buffered saline (PBS)) or a placebo (same volume of PBS, 10% of alcohol) is administered by the intraperitoneal route from day D0. In this experiment and in the following experiments, the results are given for two footpads of 2–3 mice per group, these results being representative of three to four separate experiments. The measurement of the thickness of the footpads is carried out daily in accordance with the protocol provided in R. M. Zinkernagel, T. Leist, H. Hengartner and A. Althage, J. Exp. Med. 162, 2125 (1985) (FIG. 1A).

Figure 1B:
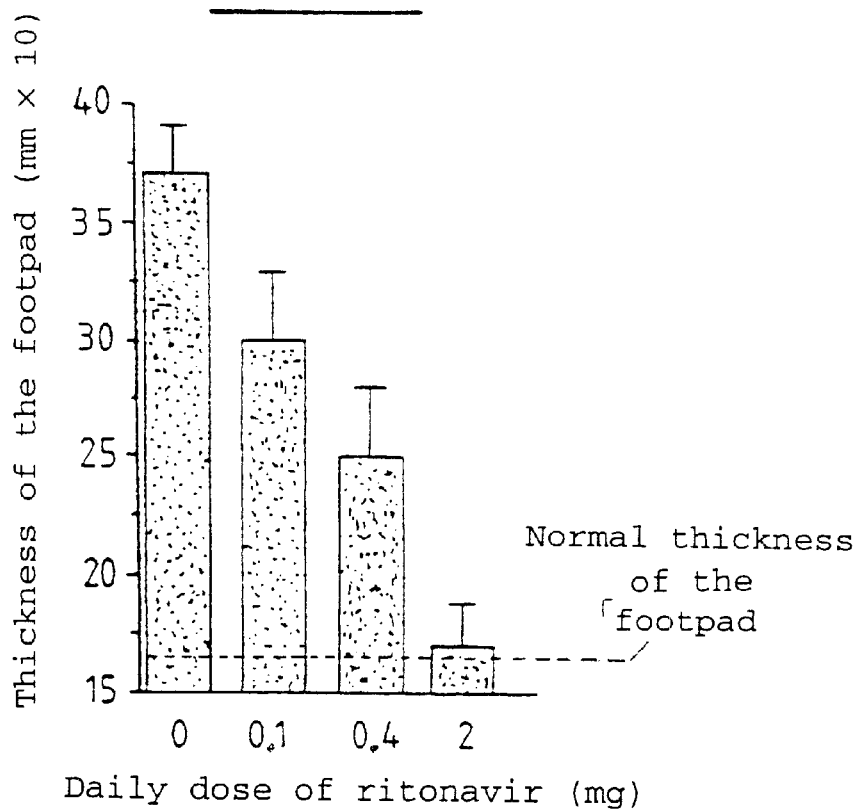
FIG. 1B represents the thickness of the footpad of mice at the $8^{th}$ day after the beginning of the treatment with ritonavir, the daily doses of ritonavir being variable.

The swelling of the footpad induced by infection with LCMV was measured on day D8 in the mice treated with variable doses of ritonavir (FIG. 1B).

Results:

The C57BL/6 mice into which the LCMV-WE virus was injected exhibited, after seven to eight days, a swelling of the footpad which is a direct measurement in vivo of the activity of the cytotoxic T lymphocytes. This swelling was markedly inhibited by treatment with ritonavir, in a dose-dependent manner. Similar results were obtained using various viral strains (LCMV-Docile strain 10 pfu/ml obtained form C. Pfau, Troy or LCMV-Armstrong strain $10^4$ pfu/ml obtained form M. Buchmeier La Jolla), with mice of different haplotypes (BALB/c; $H2^d$), and whether the route of administration is parenteral or oral (with an intragastric probe).

2. Inhibition of the Cytotoxic T Lymphocyte Activity In Vivo

Figure 1C:
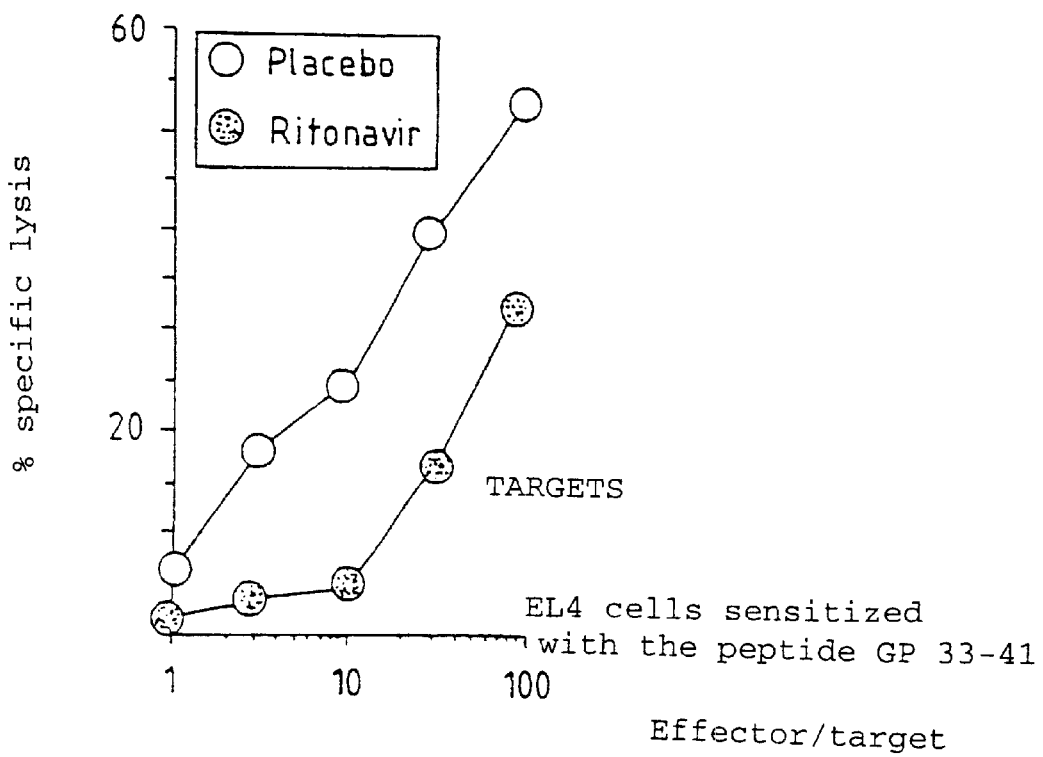
FIG. 1C represents the percentage of specific lysis of the EL4 target cells sensitized with the peptide GP33–41 by lymphocytes isolated from the spleen of mice treated or not treated with ritonavir.
Figure 1D:
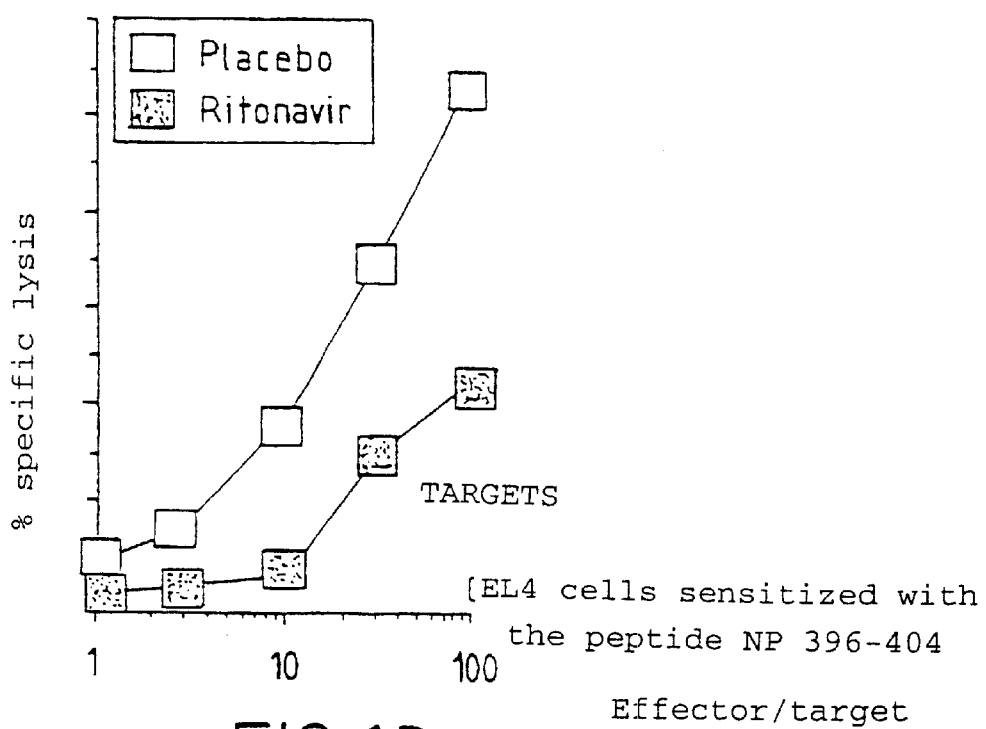
FIG. 1D represents the percentage of specific lysis of the EL4 target cells sensitized with the peptide NP 396–404 by lymphocytes isolated from the spleen of mice treated or not treated with ritonavir.

Method:

C57BL/6 mice treated with ritonavir (1.25 mg/mouse/day) or with a placebo were infected with 200 pfu of LCMV-WE by the intravenous route. Eight days after infection, the splenocytes were collected and tested for lysis of the EL4 cells ($H-2^b$) sensitized with 500 nM of the peptide GP33–41 (amino acids 33 to 41 of the LCMV glycoprotein, that is KAVYNFATC; FIG. 1C) or of the peptide NP 396–407 (amino acids 396 to 407 of the LCMV glycoprotein, that is EQPQNGFIH; FIG. 1D).

Results:

The treatment with ritonavir inhibited the cytotoxic T lymphocyte response to a systemic infection by the LCMV virus. The lysis of the target cells was reduced when the mice received the treatment with ritonavir.

3. Inhibition of the Proliferation of the $CD8^+$ T lymphocytes In Vivo

Method:

Mice were infected with 200 pfu of LCMV-WE by the intravenous route and treated with ritonavir or a placebo as described above. The splenocytes were identified with an anti-CD8 antibody conjugated with FITC (Pharmingen, San Diego) and analysed by FACS.

Figure 1E:
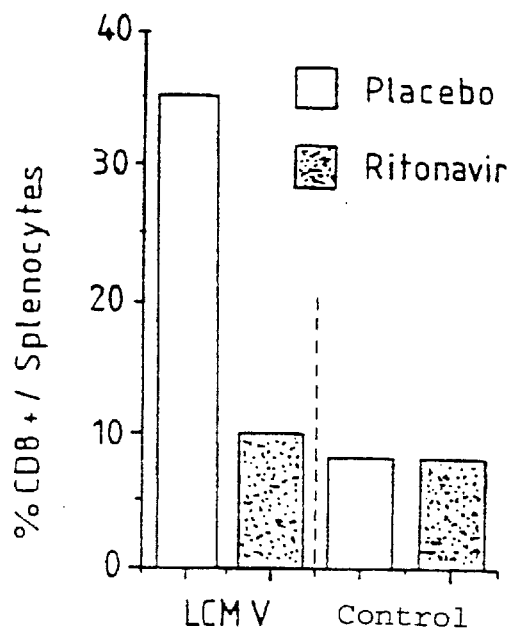
FIG. 1E represents the percentage of $CD8^-$ cells relative to the total number of splenocytes, in the case of mice infected or not infected with the LCMV virus, and treated or not treated with ritonavir.

Results:

Inhibition of the proliferation of the $CD8^+$ T lymphocytes normally observed in response to the LCMV virus is observed (FIG. 1E).

4. Effect of Ritonavir on the LCMV Load

Method:

Mice were infected with an LCMV virus (200 pfu) by the intrevenous route and treated with ritonavir or a placebo as described in point 2 above. The titre of viruses in the spleen was determined on day D8, in accordance with the protocol described in Battegay et al., J. Virol. Methods, 33, 191 (1991).

Figure 1F:
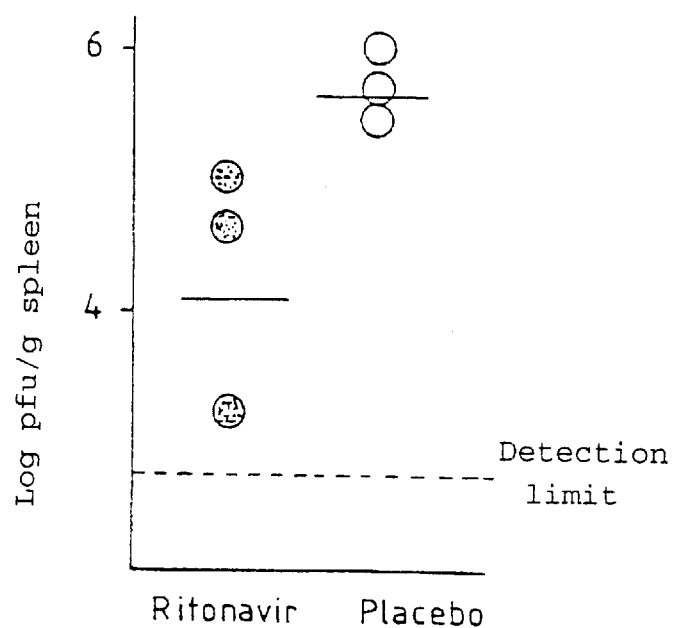
FIG. 1F represents the effect of ritonavir on the LCMV viral load.

Results:

The reduction of the lysis of the target cells as observed above is accompanied by a decrease in the viral clearance (FIG. 1F), a result which confirms that ritonavir acts directly on the immune response rather than indirectly by an antiviral effect on LCMV.

5. Evaluation of the Antibody Response Method:

The antibodies specific for the LCMV nucleoprotein and for the LCMV glycoprotein were evaluated after four and eight weeks by an ELISA test as described in O. Planz, P. Seiler, H. Hengartner and R. M. Zinkernagel, Nature, 382, 629 (1990).

Results:

Ritonavir does not reduce the capacity for synthesizing anti-virus antibodies.

EXAMPLE 2

Figure 2A:
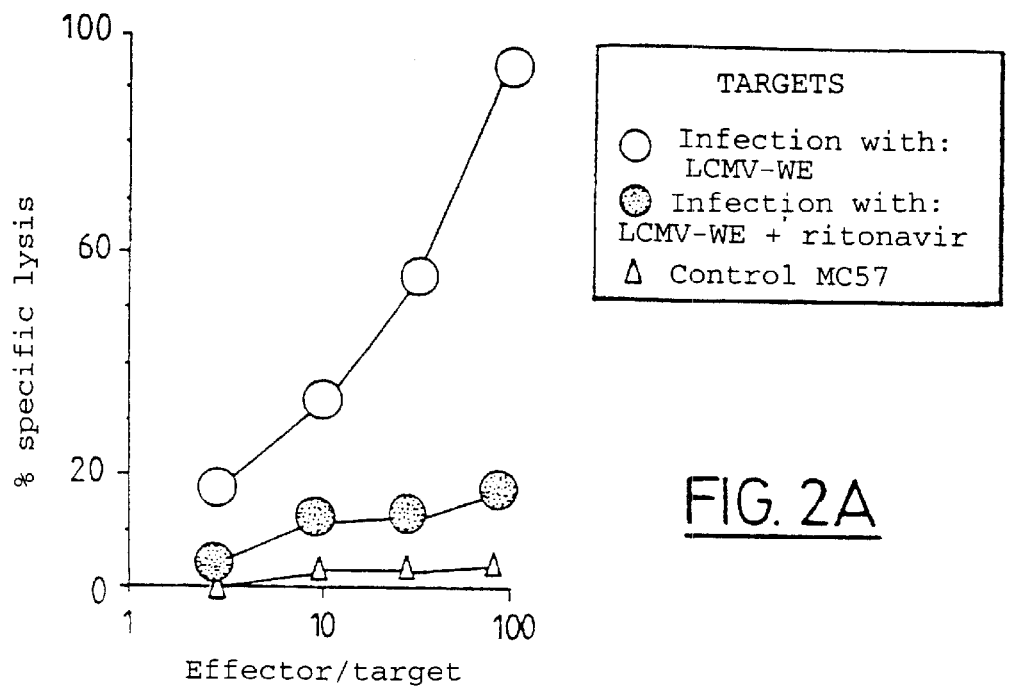
FIG. 2A represents the percentage of specific lysis of the target cells (fibroblasts MC57 infected with LCMV) incubated in the presence or in the absence of ritonavir, by anti-LCMV cytotoxic T lymphocytes.
Figure 2B:
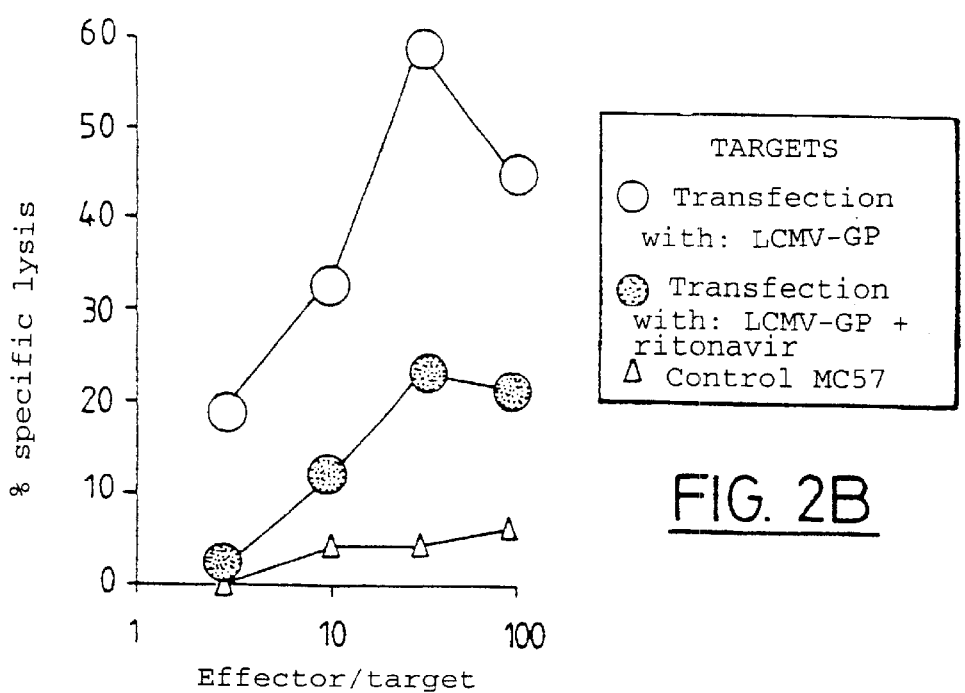
FIG. 2B represents the percentage of specific lysis of the target cells (fibroblasts MC57 transfected with the glycoprotein GP) incubated in the presence or in the absence of ritonavir, by anti-GP cytotoxic T lymphocytes.

Effect of Ritonavir on the Presentation of the Antigenic Peptides by the MEC Class 1 to Mouse Cytotoxic T Lymphocytes 1. Effect of Ritonavir on the Cycototoxic T Lymphocyte Mediated Lysis of the Target Cells Infected with LCMV-WE and Treated In Vitro with Ritonavir Method:

Cytotoxic T lymphocytes were prepared from splenocytes of mice infected with LCMV and restimulated in vitro by sensitized cells, either with the peptide GP33–41 (FIG. 2A) or with the peptide NP396–404 (FIG. 2B).

Their cytolytic activity was tested for against MC57 fibroblasts ($H-2^b$) infected with LCMV at a multiplicity of infection of 0.04 and incubated or otherwise in the presence of ritonavir at 5 µg/ml for 36 hours.

The direct effect of ritonavir on the cytotoxic T lymphocytes in vitro was excluded by extensively washing the target cells before the lysis test.

Results:

These in vitro studies on viral antigen presenting cells after infection with a virus indicate that the inhibition of the cytotoxic T lymphocyte responses occurs at the level of the presentation of the antigen. The incubation of the MC57 cells, infected with the LCMV virus, with ritonavir strongly inhibits lysis by the anti-LCMV cytotoxic T lymphocytes (FIG. 2A). A similar inhibitory effect was also observed on MC57 cells treated with ritonavir and expressing, upon transfection, the LCMV glycoprotein (FIG. 2B).

EXAMPLE 3

Figure 3A:
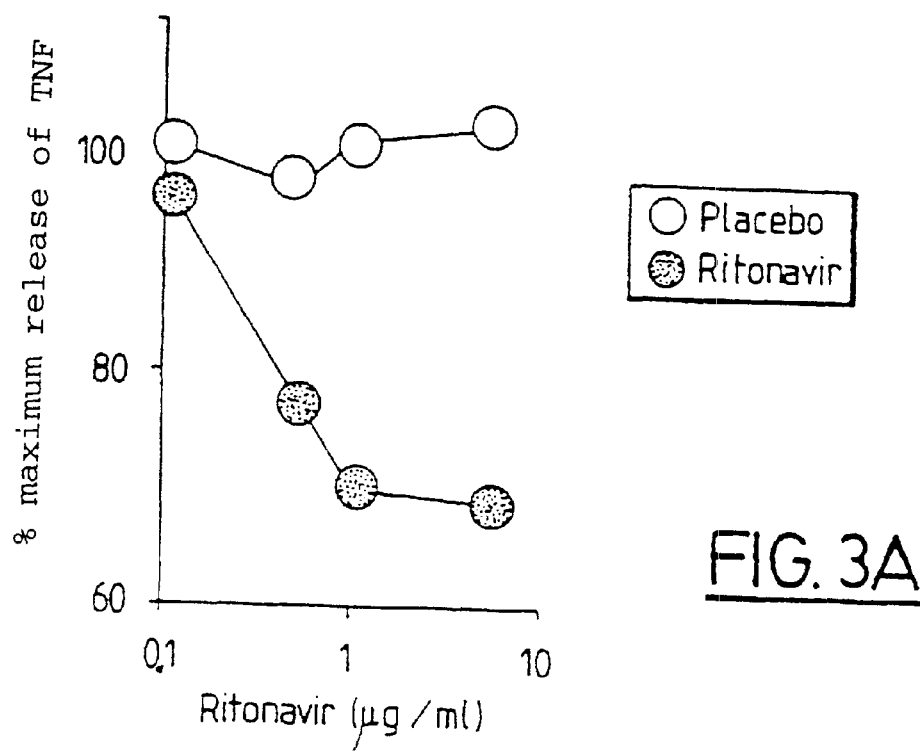
FIG. 3A represents the maximum percentage of release of TNFα as a function of the ritonavir dose used.
Figure 3B:
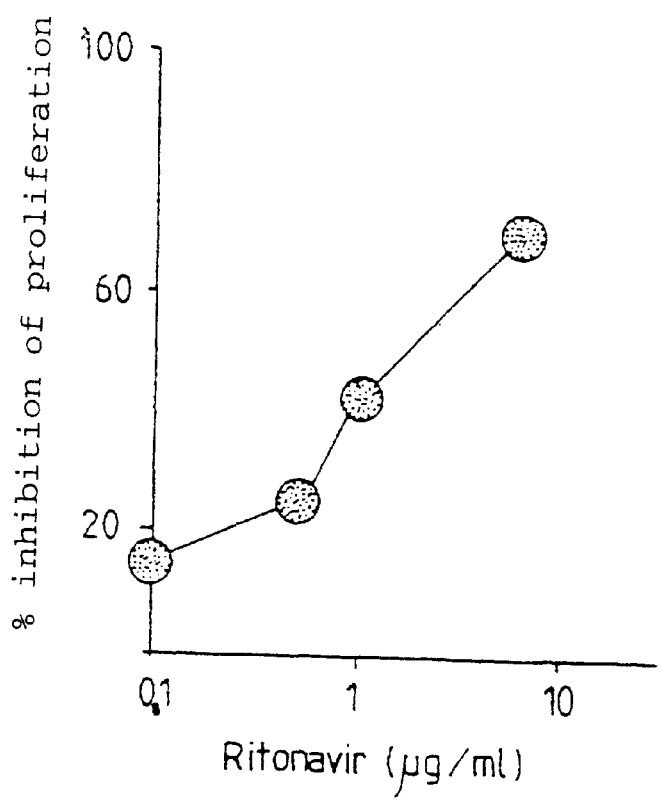
FIG. 3B represents the percentage inhibition of the proliferation of T lymphocytes M77–84 as a function of the ritonavir dose used.

Effect of Ritonavir on the Presentation of Antigenic Peptides by the MRC I to Human T Lymphocyte Clones Method:

a) In this experiment, M113 and M77–84 cells were used which are respectively a melanoma line HLA-A2 presenting the MART-1 antigen and a CD8+ cytotoxic T lymphocyte clone recognizing this antigen (Y. Kawakami et al., J. Exp. Med., 180, 347 (1994); N. Gervois, Y. Guilloux, E. Diez, and F. Jotereau, J. Exp. Med., 183, 2403–7 (1996)). The M113 cells were cultured for 24 hours with various concentrations of ritonavir and then resuspended and fixed in paraformaldehyde. As control, the same concentrations of indinavir were used. The production of TNFα by the responsive M77–84 T lymphocytes in the supernatant was measured and is expressed in FIG. 3 as a percentage of maximum release obtained with the untreated M113 cells.

b) The M113 cells were cultured for 24 hours in the presence of ritonavir (0.1–5 µg/ml) and then used as stimulators in a test of proliferation with the M77–84 T lymphocytes as responsive cells. The proliferation was measured after 48 hours in the presence of thymidine added at 1 µCi/well during the last eighteen hours (FIG. 3B).

Results:

These experiments using clones of human cytotoxic T lymphocytes directed against melanoma antigens gave results similar to the preceding experiments presented above. FIGS. 3A and 3B show the inhibition of the presentation of the human melanoma MART-1 antigen by cells growing in the presence of ritonavir to CD8+ T lymphocytes. The inhibition is dose-dependent and is effective at therapeutic doses, as was observed when the antigen presenting cells are cultured in serum obtained from HIV-negative volunteers after ingestion of a single oral dose of 500 mg of ritonavir. Up to 70% inhibition of proliferation was observed with sera obtained 3 hours after ingestion, corresponding to the plasma ritonavir concentration peak.

EXAMPLE 4

Effect of Ritonavir on the "Chymotrypsin-like" Activity of the Proteasome

1. Effect of Ritonavir on the Degradation of the Proteins with a Short Lifespan

Figure 4A:
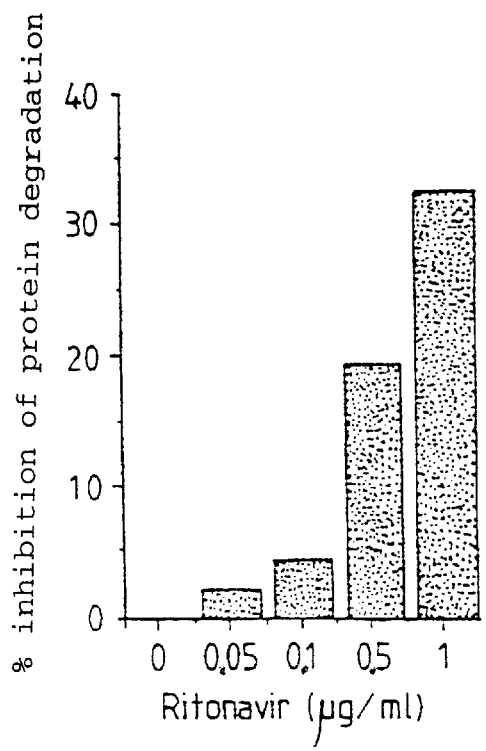
FIG. 4A represents the percentage inhibition of the degradation of proteins with a short lifespan as a function of the ritonavir dose used.

Method:

For these analyses, the cells were cultured overnight in the presence of a variable concentration of ritonavir, preincubated in a medium free of methionine and cysteine for 1 hour, subjected to labelling with $^{35}$S-methionine and $^{35}$S-cysteine for one hour, washed in PBS and subjected to a chase for one hour. After one hour, TCA (trichloroacetic acid at 10% final) was added to the supernatant and the radioactivity of the supernatant not precipitated with TCA was quantified with a Lumaplate (Topcount Packard) (FIG. 4A).

Results:

Ritonavir inhibits in a dose-dependent manner the degradation of proteins with a short lifespan, a method known to be mainly dependent on the ubiquitin proteasome pathway. These results strongly suggest that the proteasome activity is modified by ritonavir.

2. Effect of Ritonavir on the Proteasome

Figure 4B:
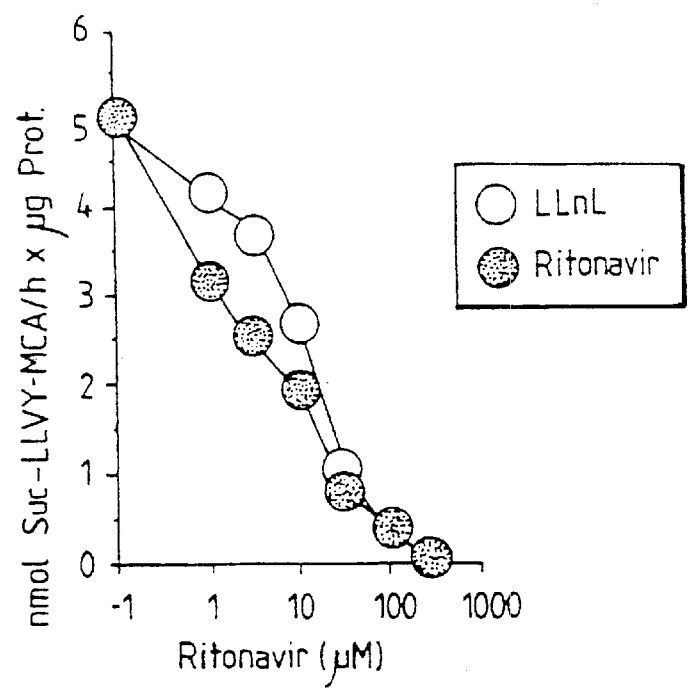
FIG. 4B represents the hydrolysis of a fluorogenic substrate Suc-LLVY-MCA by the proteasome as a function of the ritonavir dose used.
Figure 4C:
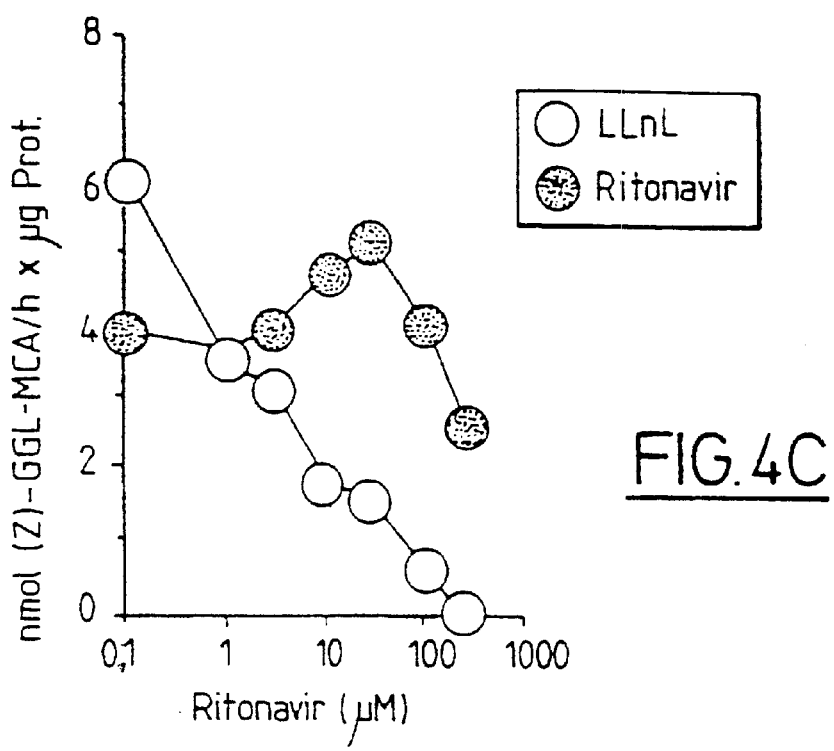
FIG. 4C represents the hydrolysis of a fluorogenic substrate (Z)-GGL-MCA by the proteasome as a function of the ritonavir dose used.
Figure 4D:
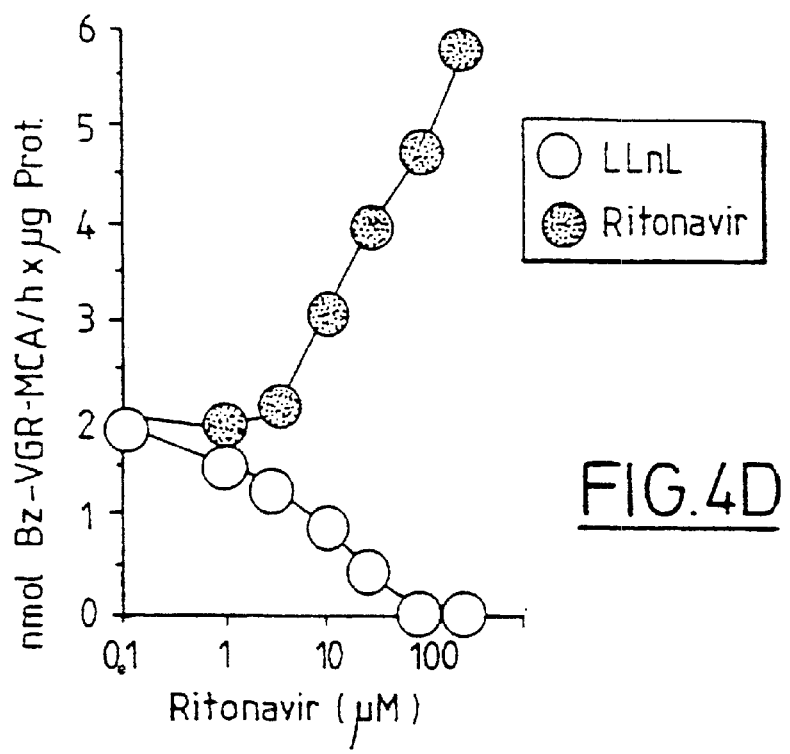
FIG. 4D represents the hydrolysis of a fluorogenic substrate Bz-VGR-MCA by the proteasome as a function of the ritonavir dose used.

Method:

FIGS. 4B, 4C and 4D show the hydrolysis of the fluorogenic substrate (100 μM Suc-LLVY-MCA, 100 μM (Z)-GGL-MCA and 400 μM Bz-VGR-MCA) of the 20S proteasomes isolated from murine B8 fibroblasts, as a function of variable concentrations of ritonavir and of LLnL (N-acetyl-L-leucinyl-L-leucinal-L-norleucinal, known inhibitor of the proteasome). The results are reported for one hour of digestion with the 20S proteasome (500 ng) in a final volume of 100 μl. The values were located in a linear detection domain and are the mean values of triplicates with standard errors of less than 3%.

Results:

The results presented in FIGS. 4B, 4C and 4D show that ritonavir is a potent inhibitor of proteasome-mediated hydrolysis of the fluorogenic substrate Suc-LLVY-MCA (cleavage on the carboxyl side of tyrosine). By contrast, the hydrolysis of the substrate (Z)-GGL-MCA (cleavage on the carboxyl side of leucine) was hardly affected, and the cleavage of the substrate Bz-VGR-MCA (cleavage on the carboxyl side of arginine, with a "trypsin" type activity) was substantially increased. This selective inhibition by ritonavir is in contrast with the inhibition by the peptide aldehyde LLnL of the proteasome, known to covalently block all the active sites of the 20S proteasomes, and which inhibits in a similar manner the proteolysis of the three fluorogenic substrates tested (V. Cerundolo et al., Eur. J. Immunol. 27, 336 (1997): A. Vinitsky et al., J. Immunol. 159, 554 (1997); M. Groll et al., Nature, 386, 463 (1997).

The maturation of the class I molecules in the endoplasmic reticulum in order to acquire resistance to endoglycosidase-H and the expression at the surface of the class I molecules were not significantly blocked by a treatment with ritonavir, which is in agreement with a selective inhibition.

3. Comparison of Four Onhibitors of HIV-1 Protease

Figure 4E:
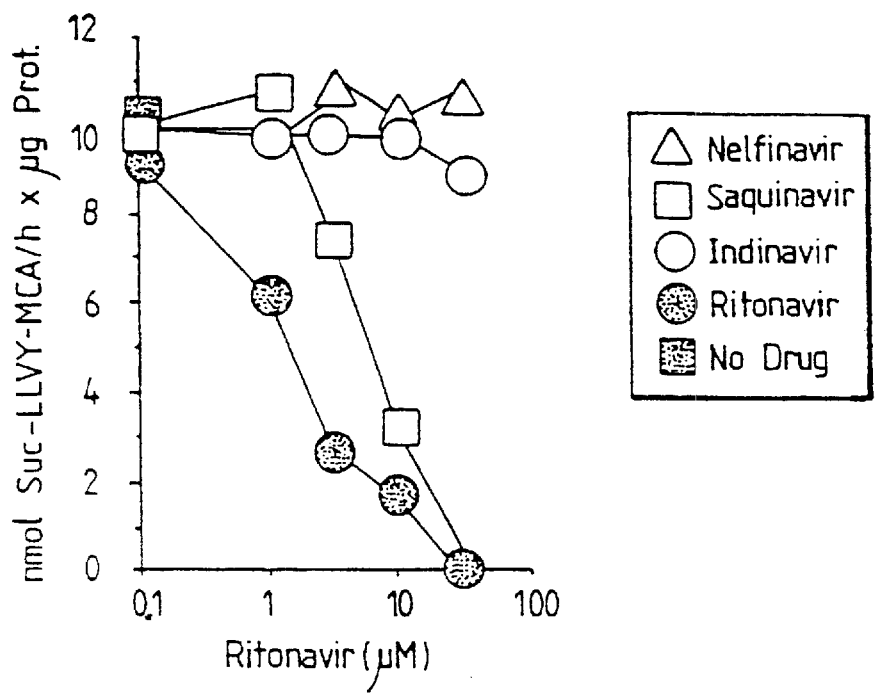
FIG. 4E represents the hydrolysis of the fluorogenic substrate Suc-LLVY-MCA by the proteasome, in the presence of nelfinavir, saquinavir, indinavir or ritonavir.

Method:

The hydrolysis of Suc-LLVY-MCA by the 20S murine proteasomes was tested according to the method described in Example 4.2. under identical conditions except for the fact that a different batch of purified proteasomes was used. The hydrolysis of Suc-LLVY-MCA was measured in the presence of increasing concentrations of ritonavir, nelfinavir (Roche), saquinavir (mesylate) and indinavir (active ingredient of Crixivan® marketed by Merck and Sharp and Dohme). The HIV protease inhibitors were dissolved beforehand in ethanol, methanol, DMSO and water respectively, for use in vitro (FIG. 4E).

Results:

Apart from ritonavir, saquinavir mesylate inhibits the "chimotrypsin-like" activity, whereas no inhibition is observed with indinavir and nelfinavir. The swelling of the footpad after injection of LCMV and the direct lysis ex vivo after systemic infection were not inhibited by indinavir or nelfinavir. By contrast, inhibition of the swelling of the footpads can be observed with saquinavir (up to 73% inhibition on the 7th day after the treatment with an oral dose of 4 mg per day of saquinavir).

In conclusion, the specific and selective inhibition of the proteasome with ritonavir as well as with saquinavir would explain the modulatory effects of the antigen presentation observed in vivo.

Conclusion:

Mice infected by injection of LCMV into the footpad develop local inflammation with reactive oedema which is in direct relationship with the intensity of the cytotoxic T lymphocyte response. The mice no longer suffer from an inflammatory reaction at the site of injection when they receive ritonavir by the intraperitoneal or oral route and the number of splenic CD8 T lymphocytes is not increased in the treated mice. The splenocytes of these treated mice have a very weak cytolytic activity towards target cells sensitized by the LCMV peptides. Simultaneously, the clearance of the viruses is delayed and reduced.

Studies in vitro with infected or transfected and tumour cells indicate that the modulation of the cytotoxic response is exerted at the level of the presentation of the antigens. The action of these inhibitors is observed both with human or murine cells and at concentrations obtained with the therapeutic doses given during infections with the human immuno-deficiency virus.

In vitro, the degradation of the proteins with a short lifespan, a phenomenon mainly brought about by the proteasome, is decreased in the presence of ritonavir. The purified preparations of proteasome modify their enzymatic activity in the presence of ritonavir. The genesis of endogenous peptides capable of binding to the major histocompatibility complex class I (MHC-1) is therefore modified, which causes modification of the recruitment and stimulation of the CD8 T lymphocytes. The action of ritonavir was observed with various human or murine antigen presenting cells in relation to various CD8 T cells. Modification of the enzymatic activity of the proteasome is also observed with saquinavir mesylate.

EXAMPLE 5

Effect of Ritonavir in the Treatment of Type 1 Diabetes

Method:

Ritonavir (0.6 mg per 10 g of body weight per day) or a placebo (phosphate buffer PBS) was administered by the intraperitoneal route to NOD mice. The pancreatic islets were removed and cultured for 24 hours in the presence or in the absence of 2.5 µg/ml of ritonavir. The cells were then cocultured with MHC-1-restricted hybridomas (FT6.9 and FT7.9 for 24 hours). The quantity of IL-2 was assayed in the supernatant.

Results:

The following tables present the quantities of IL-2 measured by a test of proliferation (cpm×$10^{-3}$).

a) Hybridoma ETG.9 (MHC-I)

|  | IN VITRO | |
| --- | --- | --- |
|  | PBS | Ritonavir |
| IN VIVO |  |  |
| PBS | 64 (0%) | 40 (37%) |
| Ritonavir | 34 (47%) | 44 (31%) | b) Hybridoma FT7.9 (MHC-I)

|  | IN VITRO | |
| --- | --- | --- |
|  | PBS | Ritonavir |
| IN VIVO |  |  |
| PBS | 92 (0%) | 43 (53%) |
| Ritonavir | 70 (24%) | 74 (20%) |

In this NOD murine diabetes model, the Langerhan's cells isolated from mice treated with ritonavir are no longer recognized ex vivo by cytotoxic T clones.

Figure 5:
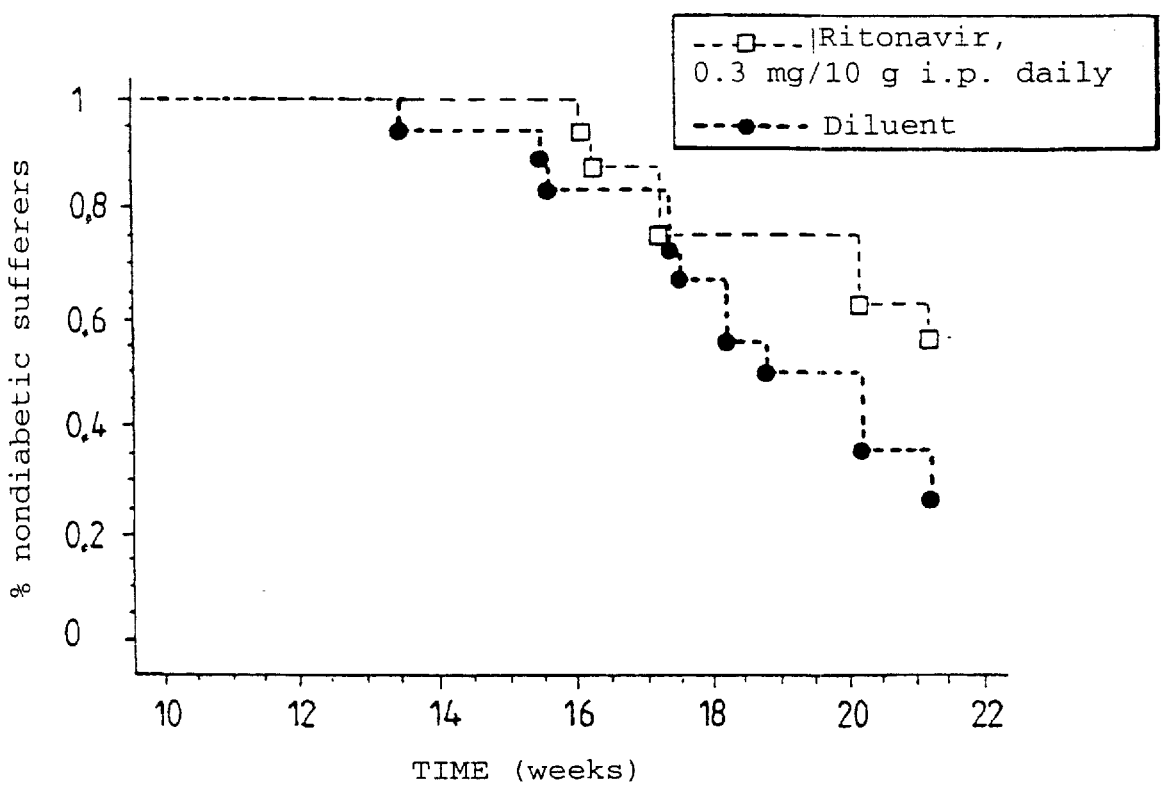
FIG. 5 represents the percentage of nondiabetic NOD mice as a function of time, in the case of a treatment with ritonavir compared with administration of a diluent.

In addition, as shown in FIG. 5, the treatment with ritonavir delays the appearance of type 1 diabetes in NOD mice.

EXAMPLE 6

Effect of Ritonavir in the Treatment of Experimental Allergic Encephalitis in Rats and Mice, Human Multiple Sclerosis Model a) in rats:

Method:

Experimental allergic encephalitis in rats is the only model of multiple sclerosis in humans. The guinea pig MBP (Myelin Basic Protein) is administered to 7-week old female Lewis rats by a subcutaneous injection, into the footpad, of 50 µg of MBP in 100 µl of complete Freund's adjuvant supplemented with 4 µg/ml of mycobacteria. There are administered, in addition, to these rats, daily, either 1 mg, 5 mg or 10 mg of ritonavir, per animal, or a placebo (phosphate buffer) of MBP injection until the animals not treated with ritonavir are killed. The clinical scores measuring the progression of the experimental allergic encephalitis are the following:

1: weakness of the movements of the tail;
2: incomplete paralysis of the hindquarters;
3: complete paralysis of the hindquarters;
4: incomplete paralysis of the forequarters; and
5: total immobility.

About eight days after this immunization with MBP, the control rats started to show the first stages of paralysis (temporary) due to the immune response caused by the administration of myelin.

Figure 6:
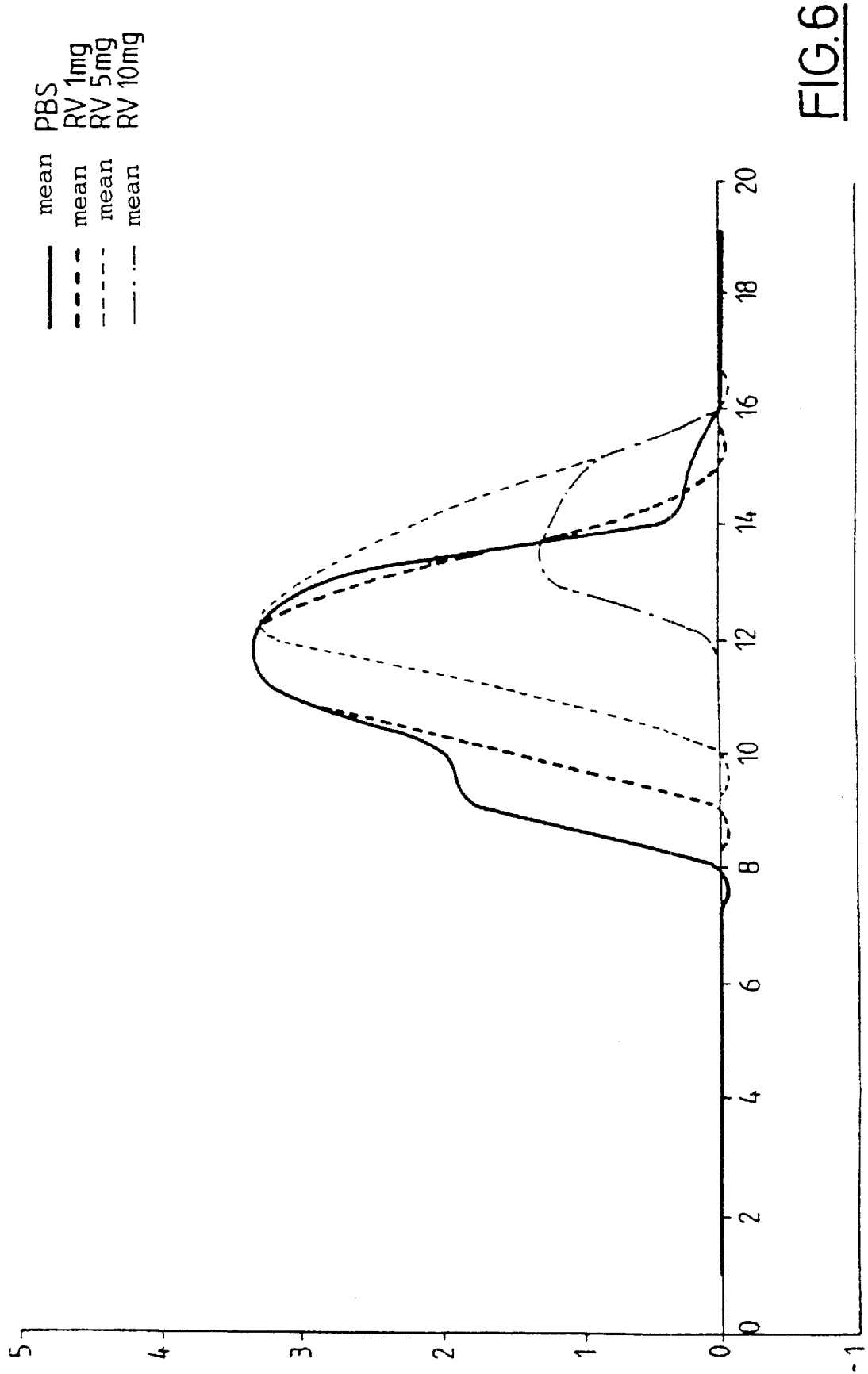
FIG. 6 represents the clinical scores for rats suffering from experimental allergic encephalitis (EAE), treated with ritonavir.

Results:

The appearance of the first signs of paralysis is delayed in the rats treated with ritonavir (1 and 5 mg). Among the rats treated with 10 mg of ritonavir, two did not develop the disease, and the other rats only exhibited the attenuated symptoms of EAE (clinical score: 1) (FIG. 6).

b) in mice:

Results similar to those described in rats were obtained in mice. Additional information was recorded which showed the possibility of a transfer of the protection induced by ritonavir.

Methods and results:

In this experiment, healthy recipient mice not treated with ritonavir received, by the intravenous and/or peritoneal route, cells of the lymph nodes and of the spleen obtained from donor mice treated with ritonavir and having been subjected to the protocol for induction of EAE described above in Example a) and adapted to mice.

The popliteal, inguinal and mesenteric ganglia and the spleen are removed at D10 after injection of MBP, cultured in the presence of 50 µg/ml of MBP. On the third day of culture, the nonadherent cells are recovered, passed over Ficoll and injected into the recipient mice ($10 \times 10^6$ injected cells). The protocol for induction of EAE at D30 after the transfer of the cells causes no symptom of EAE in these recipient animals.

Conclusion:

The treatment with ritonavir protects the mice and the rats from EAE. This protection may be transferred through the cells of the lymph nodes and of the spleen from the treated mice to recipient mice not treated with ritonavir.

EXAMPLE 7

Effect of Ritonavir in the Treatment of Hepatitis C

1. Objective

The hepatitis C virus (HCV) is the principal aetiological agent responsible for posttransfusion and sporadic non-A, non-B hepatitis. At least 70% of the infections become chronic, progressing very frequently to cirrhosis and cancer. The HCV infection is a major public health problem and the treatments based on interferon, which are the most widely used, are effective in only 25% of cases.

The anti-HCV CD8 T lymphocytes predominate in the hepatic inflammatory infiltrates during chronic infections. Their increased activation causes both a high destruction of the hepatocytes, leading to hepatic insufficiency and an immunosuppression which prevents total clearance of the virus. A specific control of the activation of the CD8 cytotoxic T lymphocytes would make it possible to attenuate the immunopathology of the HCV infection by lifting the immunosuppression and reducing the hepatic destruction.

The mechanisms responsible for hepatic damage during infection with the hepatitis C virus (HCV) are poorly known. The clinical observation that short treatments with corticosteroids reduce the serum levels of aminotransferases despite aggravation of the viremia, suggests that the immune response plays an important role in the destruction of the hepatocytes. The fact that the majority of the patients infected with HCV progresses to chronicity indicates that the presence of anti-HCV cytotoxic T lymphocytes is not sufficient to eliminate the virus. Although the CD8 T lymphocytes are present in a large number in the inflammatory infiltrates, their role both in the protection against the virus and in the destruction of the hepatic tissues remains confusing. Patients with a high anti-HCV cytotoxic T lymphocyte activity have indeed a lower viremia but they also have higher levels of transaminases and develop a more active disease (Nelson D. R. et al., J. of Immunol. 158, 1473 (1997)). By contrast, patients with a high anti-HCV CD4 response exhibit less frequently clinical and histological signs of hepatic diseases. Consequently, the balance between viral clearance and hepatic destruction is strongly linked to the relative activity of the intrahepatic populations of HCV-specific CD4 and CD8 T lymphocytes.

In a patient chronically infected with HCV, the depletion of the CD8 T lymphocytes by anti-CD8 monoclonal antibodies has beneficial effects (Kiefersauer S, et al., J. of Immunol., 159, 4046 (1997)). After this treatment, the transaminases were greatly reduced, the hepatic information was reduced and the proliferative response to the HCV antigens was restored. Tsai et al. also showed that the in vitro depletion of the CD8 T lymphocytes from peripheral blood allowed a proliferative response to the HCV antigens (Tsai et al., J. Hepatol. 21, 403 (1993)).

The proliferative response is a determining element of the viral clearance during the acute infection phase and a high CD4 T response is associated with the elimination of the virus. This response is low or absent in patients progressing towards chronicity or who manifest clinical signs of chronicity (Diepolder H et al., Lancet, 346, 1006 (1995)).

The murine model of chronic infection with LCMV resembles, in certain aspects, the chronic infection with HCV. In this model, the CD8 T lymphocytes may not only hamper the elimination of LCMV, but in addition, they make the animals incapable of combating a new infection with VSV (Dunlop M and Blanden R, J. exp. Med. 145, 1131 (1977)); Odermatt B et al., Natl. Acad. Sci. USA 88, 8252 (1991)). The depletion of the CD8 T lymphocytes by anti-CD8 monoclonal antibodies is accompanied by complete restoration of the immune Zinkernagel, J. Exp. Med. 167, 1749 (1988)). Furthermore, the cytotoxic T lymphocytes can destroy the infected cells such as the antigen presenting cells, the T lymphocytes and the B lymphocytes producing neutralizing antibodies which are essential for developing a protective response (Odermatt B et al., Natl. Acad. Sci. USA 88, 8252 (1991); Leist T. P., E. Ruedi and R. M. Zinkernagel, J. Exp. Med. 167, 1749 (1988)).

The modulation of the anti-HCV CD8 activity may therefore be a good strategy for promoting the development of a protective humoral immunity.

2. Clinical Case

Profound modifications of the CD8 cytotoxic T response open a novel therapeutic route for chronic infections with noncytopathogenic viruses. Indeed, the example LCMV shows that the use of ritonavir in the chronic infection with the hepatitis C virus ought to bring about a reduction in the cytotoxic response and immunopathological effects with favourable clinical consequences.

Figure 7:
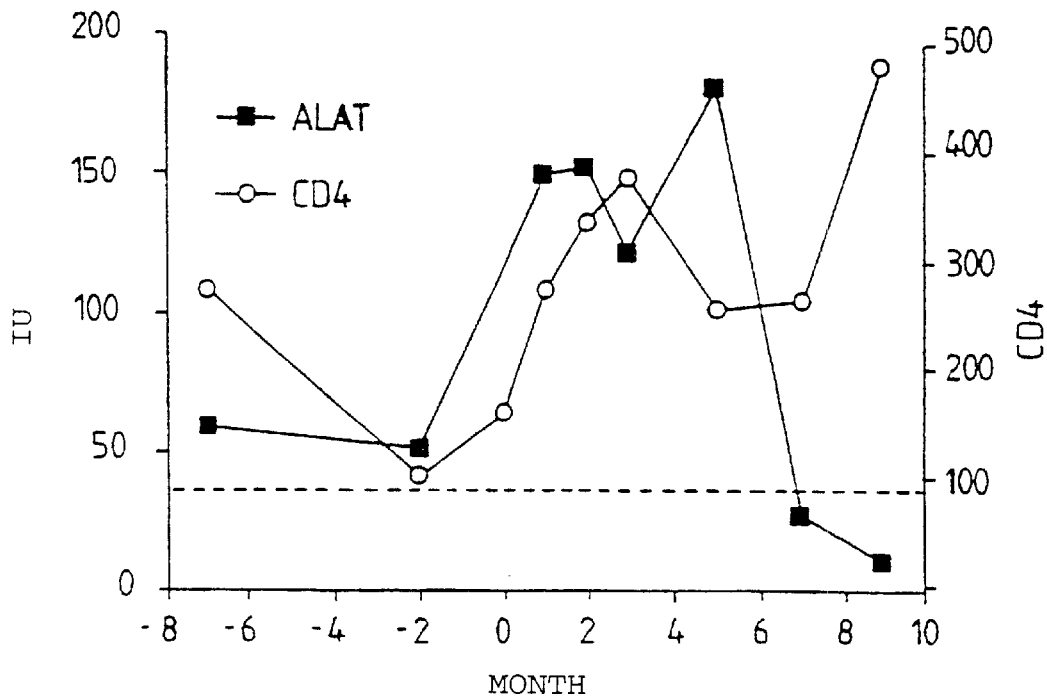
FIG. 7 represents the progression of chronic infection with the hepatitis C virus in a patient infected with HIV and treated with ritonavir.
Figure 7:
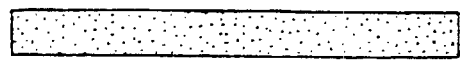

A patient who is a drug addict is monitored for a double infection with HIV and HCV, discovered in 1986 but undoubtedly prior to this date. The progression of the HIV infection is slow, with a viremia established at around 4 Log HIV RNA copies/ml. The level of CD4 T lymphocytes dropped with a first opportunistic lung infection. The HCV viremia oscillated around 5 to 6 Log HCV RNA copies/ml and the serum transaminase level was moderately high (2 or 3 times the normal value). An HIV protease inhibitor, ritonavir, was introduced into the therapy of the patient and followed since then. The HIV viremia became undetectable during the two months which followed the beginning of the treatment before returning to the previous level from the fourth month. The level of CD4 T lymphocytes increased during this period and continued to increase even after the reappearance of the HIV viremia. By contrast, the HCV viremia became negative at the 7th month after the introduction of ritonavir (FIG. 7), and has remained so two years later.

3. Retrospective Study of the Progression of the HCV Infection in AIDS Patients Treated With Ritonavir or With Indinavir In patients infected with HIV-1, the effect of ritonavir on the immune response may result from its antiretroviral activity and from the reduction of the activity of the cytotoxic T lymphocytes (CTL) and the immunopathology. A retrospective study of patients coinfected with the HCV and HIV viruses was carried out in order to compare the HCV viral load, the hepatic function and the anti-HCV antibody titre in patients receiving ritonavir and saquinavir or indinavir during the first four months of the therapy. The patients enrolled (41) had a chronic HCV infection proven by the presence of anti-HCV antibodies and of serum HCV RNA detected by RT-PCR. Eighteen patients received ritonavir alone (that is 600 mg twice per day), three received ritonavir and saquinavir (800 mg per day), 20 received indinavir (800 mg three times per day). The control population consisted of 105 patients with no detectable anti-HCV or anti-HBV antibodies and with no opportunistic infection, but receiving ritonavir for the first time for at least four months.

Initially, the coinfected patients showed the clinical symptoms, a viral HIV load, a T lymphocyte number and biological values which were similar. A moderate hepatic cytolysis existed in both groups (87+/−61 IU/1 for indinavir and 54+/−28 IU/1 for ritonavir). The viral HCV loads and the HCV genotype distribution between the two groups were similar. In the infected patients, the ALAT concentrations increased more frequently in those taking ritonavir (57%; 12/21 patients) than in those taking indinavir (10%; 2/20 patients; p<0.002). In the ritonavir group, it was possible to observe an ALAT concentration peak during the third month with a mean maximum value of 418 IU/1 (variation: 96–1570).

In the control population, an increase in the ALAT concentrations was observed in only 12 patients out of 105 (11.4%, p=$10^{-6}$) indicating that the very high frequency of patients infected with HCV and suffering from a cytolytic hepatitis during the treatment with ritonavir is not linked to the toxicity of the medicament but results from its action on the cells infected with HCV either directly or by the modulation of the immune response.

Table 1 below presents a comparison of the biological markers for patients infected with HCV with or without an increase in the transaminases during the treatment with ritonavir (groups I and II respectively) and in the patients treated with indinavir without elevation of ALAT (group III).

Statistical calculations with group IV were not carried out because of the small number of patients. This involved two patients with a cytolytic hepatitis associated with a substantial increase in the viral HCV load (+3.57 $\log_{10}$ of copies of RNA/ml in one patient and +0.5 $\log_{10}$ of copies of RNA/ml in the second patient).

The variations in the HCV RNA concentrations and in the antibody indices were measured on preserved pairs of serum (10 pairs in group I, 6 in group II, 10 in group III and 2 in group IV). The sera were initially collected and at weeks 6.8 and 7.2 for groups I and III respectively (p>0.2). The HIV and HCV RNA concentrations are presented in the form of $\log_{10}$ of copies of RNA/ml and the T lymphocyte numbers in the form of cells /mm$^3$. The ALAT concentrations are expressed in international units/l.

The anti-HCV antibodies were quantified using version 3.0 of the Axsym HCV system (Abott) and the variations of the anti-HCV antibody titres of the sera of patients (Ab index) are expressed by the ratio of the optical densities.

The variations in the viral HIV load and in the T lymphocyte number were similar in the three groups I, II and III. The viral HCV load increased in all the groups with +0.61 $\log_{10}$ of copies of RNA/ml for group I compared with +0.41 $\log_{10}$ of copies of RNA/ml in group III (p<0.1) and +0.22 $\log_{10}$ of copies of RNA/ml in group II (p=0.065). An increase in the production of anti-HCV antibodies was observed only in group I (p<0.05 between groups I and III).

Thus, the antibody titre increases only in the patients exhibiting cytolysis during the therapy with ritonavir. No increase in the antibody titres was detected under indinavir even when a high increase in the HCV viremia was observed, indicating that an abundant antigenic stimulation is not sufficient to stimulate the anti-HCV humoral response. The improvement in the early humoral response during a treatment with ritonavir may be the consequence of the modulation of the CTL activity since, during infections with HBV and LCMV, it was shown that the anti-viral cytotoxic T lymphocytes lysed the B lymphocytes producing neutralizing antibodies (Planz et al., 1996, Nature, 382:726–729; Barnaba et al., 1990, Nature, 345:258–260).

The transient hepatic cytolysis observed a few days after the beginning of the treatment with ritonavir in patients suffering from hepatitis C could thus result from facilitation of apoptosis of the heptatocytes infected with HCV. This observation opens the way for the application of these molecules (ritonavir and saquinavir) for the purpose of modulation of apoptosis.

Table I: Variations of the biological values in groups of patients infected with HCV classified according to the HIV-1 protease inhibitor used and the hepatic cytolysis.

|  | Group I RTN, cytolysis + N = 12 | Group II RTN, cytolysis − N = 9 | P I versus II | Group III IDN, cytolysis- N = 18 | P I versus III | Group IV IDN, cytolysis + N = 2 |
|---|---|---|---|---|---|---|
| CD4 | 109.4(+/−113) | 88.3(+/−170) | p = 0.36 | 21.1(+/−68) | p = 0.085 | 29.5 |
| CD8 | 203.6(+/−650) | 281.8(+/−394) | p = 0.95 | 9.2(+/−222) | p = 0.22 | 203.5 |
| HCV-VL | 0.61(+/−0.3) | 0.22(+/−0.35) | p = 0.065 | 0.41(+/−0.79) | p < 0.01 | 2.25 |
| Ac index | 2.19(+/−1.68) | 0.98(+/−0.24) | p = 0.085 | 1.01(+/−0.13) | p < 0.05 | 0.98 |

N = number of individuals per group.
RTN and IDN mean ritonavir and indinavir respectively.

What is claimed is:

1. A method for treating a condition selected from the group consisting of type 1 diabetes, multiple sclerosis, hepatitis C virus and cancer, said method comprising administering to a patient in need of such treatment, an effective amount of at least one human immunodeficiency virus (HIV) protease inhibiting compound selected from the group consisting of ritonavir, saquinavir and one of their pharmaceutically acceptable salts, in combination with a pharmaceutically acceptable vehicle.

2. The method according to claim 1, wherein said administering to a patient in need of such treatment comprises administering the protease inhibiting compound one of orally, parenterally or topically, in an appropriate form thereof.

3. The method according to claim 1, wherein said administering to a patient in need of such treatment comprises administering the compound in the form of a medicament containing from 1to 2000 mg of the compound.

4. The method according to claim 1, wherein said administering to a patient in need of such treatment comprises administering the compound in the form of a medicament containing from 100 to 1500 mg of the compound.

* * * * *

UNITED STATES PATENT AND TRADEMARK OFFICE
CERTIFICATE OF CORRECTION

PATENT NO. : 6,506,555 B1
DATED : January 14, 2003
INVENTOR(S) : Andre et al.

Page 1 of 1

It is certified that error appears in the above-identified patent and that said Letters Patent is hereby corrected as shown below:

Column 15,
Lines 2-10, should read:
   1. A method for treating a condition selected from the group consisting of type 1 diabetes, multiple sclerosis and hepatitis C virus, said method comprising administering to a patient in need of such treatment, an effective amount of at least one human immunodeficiency virus (HIV) protease inhibiting compound selected from the group consisting of ritonavir, saquinavir and one of their pharmaceutically acceptable salts, in combination with a pharmaceutically acceptable vehicle.

Signed and Sealed this

Twenty-fifth Day of October, 2005

JON W. DUDAS
*Director of the United States Patent and Trademark Office*